(12) United States Patent
Soga et al.

(10) Patent No.: US 7,964,177 B2
(45) Date of Patent: Jun. 21, 2011

(54) METHOD FOR DETERMINATION OF OXIDATIVE STRESS

(75) Inventors: Tomoyoshi Soga, Yamagata (JP);
Makoto Suematsu, Tokyo (JP)

(73) Assignee: Keio University, Tokyo (JP)

( * ) Notice: Subject to any disclaimer, the term of this patent is extended or adjusted under 35 U.S.C. 154(b) by 302 days.

(21) Appl. No.: 12/161,203

(22) PCT Filed: Jan. 16, 2007

(86) PCT No.: PCT/JP2007/050517
§ 371 (c)(1),
(2), (4) Date: Sep. 4, 2008

(87) PCT Pub. No.: WO2007/083632
PCT Pub. Date: Jul. 26, 2007

(65) Prior Publication Data
US 2009/0029409 A1    Jan. 29, 2009

(30) Foreign Application Priority Data

Jan. 20, 2006    (JP) ................................. 2006-012955

(51) Int. Cl.
*A61K 49/00* (2006.01)
*G01N 33/00* (2006.01)
(52) U.S. Cl. .......................................... 424/9.1; 436/86
(58) Field of Classification Search ........................ None
See application file for complete search history.

(56) References Cited

U.S. PATENT DOCUMENTS

| | | | |
|---|---|---|---|
| 6,569,683 | B1 | 5/2003 | Ochi et al. |
| 2003/0132114 | A1 | 7/2003 | Mischak et al. |

FOREIGN PATENT DOCUMENTS

| | | |
|---|---|---|
| JP | 11-080198 | 3/1999 |
| JP | 2000-074923 | 3/2000 |
| JP | 2002-517724 | 6/2002 |
| JP | 3341765 | 8/2002 |
| JP | 2003-035698 | 2/2003 |
| JP | 2003-302396 | 10/2003 |
| JP | 2003-532115 | 10/2003 |
| JP | 2003-310621 | 11/2003 |
| JP | 2004-069672 | 3/2004 |
| WO | WO 2005/052575 | 6/2005 |

OTHER PUBLICATIONS

Kasai et al. Changes in Ophthalmic Acid and Free Amino Acid in Rats Fed With an Excess Methionine Diet; Agricultural and Biological Chemistry, vol. 53, No. 2 (1989) pp. 553-556.*

Schafer and Buettner, "Redox Environment of the Cell As Viewed Through the Redox State of the Glutathione Disulfide/Glutathione Couple," *Free Radic. Biol. Med.* 30(11):1191-1212 (2001).

European Search Report for European Patent Application No. 07706844.3, dated Jan. 12, 2009.

Soga et al., Differential Metabolomics Reveals Opthalmic Acid as an Oxidative Stress Biomarker Indicating Hepatic Glutathione Consumption, *J. Biol. Chem.*, vol. 281: 16768-76, 2006.

International Search Report (PCT/JP2007/050517) mailed Mar. 6, 2007.

Murata "Glutathione-Related Peptides" Protein, Nucleic Acid and Enzyme 33(9):1505-1512 (1988).

English language translation of Murata "Glutathione-Related Peptides" *Protein, Nucleic Acid and Enzyme* 33(9):1505-1512 (1988).

Soga et al., "Quantitative Metabolome Analysis Using Capillary Electrophoresis Mass Spectrometry," *Journal of Proteome Research* 2:488-494, 2003.

* cited by examiner

*Primary Examiner* — Rebecca E Prouty
*Assistant Examiner* — Paul C Martin
(74) *Attorney, Agent, or Firm* — Clark & Elbing LLP

(57) ABSTRACT

Provided is a biomarker that enables easy and rapid detection of oxidative stress on a living organism and enables prevention of tissue damage or cell necrosis by drug administration, and which is a powerful marker for the study of toxicity and pharmacokinetics of various agents. Oxidative stress is determined by measuring blood concentration of ophthalmic acid, which is a substance that varies in blood depending on the variation of reduced glutathione (GSH) concentration in a biological sample with the use of an analyzer such as a capillary electrophoresis-mass spectrometer. Further, an anti-oxidative stress agent is screened by administering an anti-oxidative stress candidate agent to a non-human animal under oxidative stress conditions, measuring blood concentration of ophthalmic acid, and evaluating the degree of decrease in the ophthalmic acid concentration.

4 Claims, 4 Drawing Sheets
(2 of 4 Drawing Sheet(s) Filed in Color)

METHOD FOR DETERMINATION OF OXIDATIVE STRESS

CROSS-REFERENCE TO RELATED APPLICATIONS

This application is the U.S. National Stage of International Application No. PCT/JP2007/050517, filed Jan. 16, 2007, which claims the benefit of JP2006-012955, filed Jan. 20, 2006.

TECHNICAL FIELD

The present invention relates to a method for determination of oxidative stress comprising measuring a substance whose blood concentration varies depending on oxidation-caused variation of reduced glutathione (GSH) concentration in a biological sample, and to a method for screening for an antioxidative stress agent.

BACKGROUND ART

Living organisms are continuously subjected to various stresses from outer environment. To resist such stresses, they maintain their homeostasis by various regulatory systems. Among stresses, representative is an oxidative stress caused when a living organism fails to sufficiently cope with active oxygen produced by its endogenous and exogenous causes. Against this stress, living organisms have a system called redox regulation to cope with the stress to maintain their homeostasis by regulating the redox state. This system functions to adapt to many extrinsic factors, i.e., agents, radiation, ultraviolet ray, environmental pollutants, high fever, low temperature, hypoxic condition, and infectious diseases as well as to oxidative stress from lifestyle-related diseases such as cancer, diabetes, arteriosclerosis, hypertension and obesity. However, if this regulation mechanism is broken for some reasons or become unable to provide sufficient adaptation, oxidative stress occurs. Currently, some molecular markers enabling easy examination of whether or not the intracellular redox regulation is functioning and enabling early detection of occurrence are proposed.

For example, proposed is a method for detecting oxidative stress on a living organism comprising specifically measuring oxidized apolipoprotein AI present in a sample by sandwich method using two antibodies as antibodies, one of which is an antibody specifically reacts with an oxidized site of oxidized apolipoprotein AI and the other is an antibody against apolipoprotein AI, wherein the method is available for mechanism analysis and clinical diagnosis of oxidative stress-related diseases such as arteriosclerosis and diabetes complications, e.g., nephropathy and neuropathy (for example, see Patent Document 1). Also proposed is a method utilizing, for example, a diagnostic plot of an oxidative stress profile, which is a two-dimensional coordinate system with its ordinate representing oxidative damage index calculated from oxidative damage items which shows a magnitude of oxidative damage caused by active oxygen and free radicals occurred in a living organism (generation rate of 8-hydroxy 2'-deoxyguanosine in urine per body weight, generation rate of 8-epi-prostaglandin F2α in urine per body weight, oxidation ratio of coenzyme Q10 in serum, and lipid peroxide content in serum) and with its abscissa representing a protective capacity against oxidation calculated from anti-oxidation items which shows antioxidant capacity to suppress and prevent oxidation of constituents of a living organism caused by active oxygen and free radicals occurred in a living organism, wherein values of a test subject can be filled in the plot (e.g., see Patent Document 2-4). Also proposed is a monoclonal antibody that recognizes a substance correlated with oxidative stress in a living organism and that specifically recognizes dihydropyridine structure (e.g., see Patent Document 5). However, since little is established about an indicator that can be measured from blood or urine, it was difficult to provide a living organism with prevention against oxidative stress.

On the other hand, a method for comprehensively measuring intracellular metabolites by a measuring method of metabolites in a sample with a capillary electrophoresis-mass spectrometer (CE-MS) (e.g., see Non-Patent Document 1) is a method to qualitatively and/or quantitatively determine low molecular weight compounds (metabolites) pattern and/or peptides pattern in a liquid sample from a human or animal body in order to monitor the human or animal body conditions. In this method, the metabolites and peptides in the liquid sample are separated by capillary electrophoresis, then directly ionized, and detected by an online-interfaced mass spectrometer. To monitor the human or animal body conditions for a long time, sample values and reference values representing said conditions, and the deviation obtained from such values and the correspondence between them are automatically stored in a database. For separation and analysis of anionic compounds using a combination of capillary electrophoresis and mass spectroscopy, known is a method for separation and analysis of anionic compounds wherein electroosmotic flow is reversed by a coated capillary which has a cationic ion pre-coating in its inner surface (e.g., see Patent Document 7).

[Patent Document 1] Japanese Laid-Open Patent Application No. 2004-69672
[Patent Document 2] Japanese Laid-Open Patent Application No. 2003-310621
[Patent Document 3] Japanese Laid-Open Patent Application No. 2003-302396
[Patent Document 4] Published Japanese translation of PCT international publication No. 2002-517724
[Patent Document 5] Japanese Laid-Open Patent Application No. 11-80198
[Patent Document 6] Published Japanese translation of PCT international publication No. 2003-532115
[Patent Document 7] Japanese Patent Publication No. 3341765
[Non-Patent Document 1] Soga, T., Ohashi, Y., Ueno, Y., Naraoka, H., Tomita, M., and Nishioka, T., "Quantitative Metabolome Analysis Using Capillary Electrophoresis Mass Spectrometry", J. Proteome Res. 2. 488-494, 2003.

DISCLOSURE OF THE INVENTION

Object to be Solved by the Invention

If concentration of reduced glutathione (GSH), which plays a key role in redox regulation in living organisms, can be measured at the blood level, the state of intracellular redox regulation can be easily and quickly grasped. The GSH concentration in blood, however, is infinitesimal and GSH is readily oxidized, making stable data acquisition or detection difficult. Thus, by finding a substance in blood that varies depending on the variation of GSH concentration in a tissue (in a cell) and measuring this biomarker substance, it can be determined whether or not redox regulation is functioning. If use of this predictive biomarker enables rapid detection of oxidative stress on a living organism, it is possible to administer an agent to prevent tissue damage or cell necrosis. Further, since biomarkers found in search can be an indicator for drug action of an anti-oxidative stress agent, they can be used not only for diagnosis but also for drug development, toxicity and efficacy evaluation of active oxygen removers etc. Furthermore, since intracellular glutathione is decreased by production and secretion of conjugates in drug metabolism, such biomarkers would be a powerful marker for the study of toxicity and pharmacokinetics of various agents. It is an object of the present invention to provide a biomarker that enables easy and rapid detection of oxidative stress on a living organism and enables prevention of tissue damage or cell necrosis by drug administration, and which may be a powerful marker for the study of toxicities and pharmacokinetics of various agents.

Means to Solve the Object

An agent to cause oxidative stress is administered to mice. The liver and blood of the mice is measured with an analyzer such as a capillary electrophoresis-mass spectrometer (CE-MS), high performance liquid chromatography-mass spectrometer (LC-MS), gas chromatography-mass spectrometer (GC-MS), single CE, LC, GC, mass spectrometer (MS), or nuclear magnetic resonance apparatus (NMR) to search a biomarker candidate substance in blood which varies in association with perturbation of reduced glutathione (GSH) concentration in liver which plays a key role in redox regulation. Next, if the biomarker candidate substance is identified by name and the mechanism how the substance varies in association with GSH by oxidative stress is elucidated, and support for the theoretical mechanism is obtained, then the substance would be a biomarker for oxidative stress. Accordingly, the present inventors administered acetaminophen, an oxidative stress causing agent, to mice and have found ophthalmic acid as a substance (biomarker) that varies in blood depending on the variation of GSH concentration in liver by using a method such as a capillary electrophoresis-mass spectrometer (CE-MS) which can comprehensively measure intracellular metabolites. With the above findings, the present inventors have completed the present invention.

In other words, the present invention relates to (1) a method for determination of oxidative stress comprising measuring blood concentration of ophthalmic acid, which is a substance that varies in blood depending on the variation of reduced glutathione (GSH) concentration in a biological sample; (2) the method for determination of oxidative stress according to the above (1), wherein the blood concentration of ophthalmic acid is measured with a capillary electrophoresis-mass spectrometer; (3) the method for determination of oxidative stress according to claim 1 or 2, wherein the oxidative stress is an oxidative stress originated from cancer, diabetes, arteriosclerosis, obesity, hepatitis, AIDS, Alzheimer's disease or the like.

Further, the present invention relates to (4) a method for screening for an anti-oxidative stress agent, comprising administering an anti-oxidative stress candidate agent to a non-human animal under oxidative stress conditions; measuring, before and after the administration, blood concentration of ophthalmic acid, which is a substance that varies in blood depending on the variation of reduced glutathione (GSH) concentration in a biological sample; and evaluating the degree of decrease in ophthalmic acid concentration; (5) the method for screening for an anti-oxidative stress agent according to the above (4), wherein the blood concentration of ophthalmic acid is measured with a capillary electrophoresis-mass spectrometer; and (6) the method for screening an anti-oxidative stress agent according to the above (4) or (5), wherein the anti-oxidative stress agent is a preventive or therapeutic agent for an oxidative stress-related disease originated from cancer, diabetes, arteriosclerosis, obesity, hepatitis, AIDS, Alzheimer's disease or the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
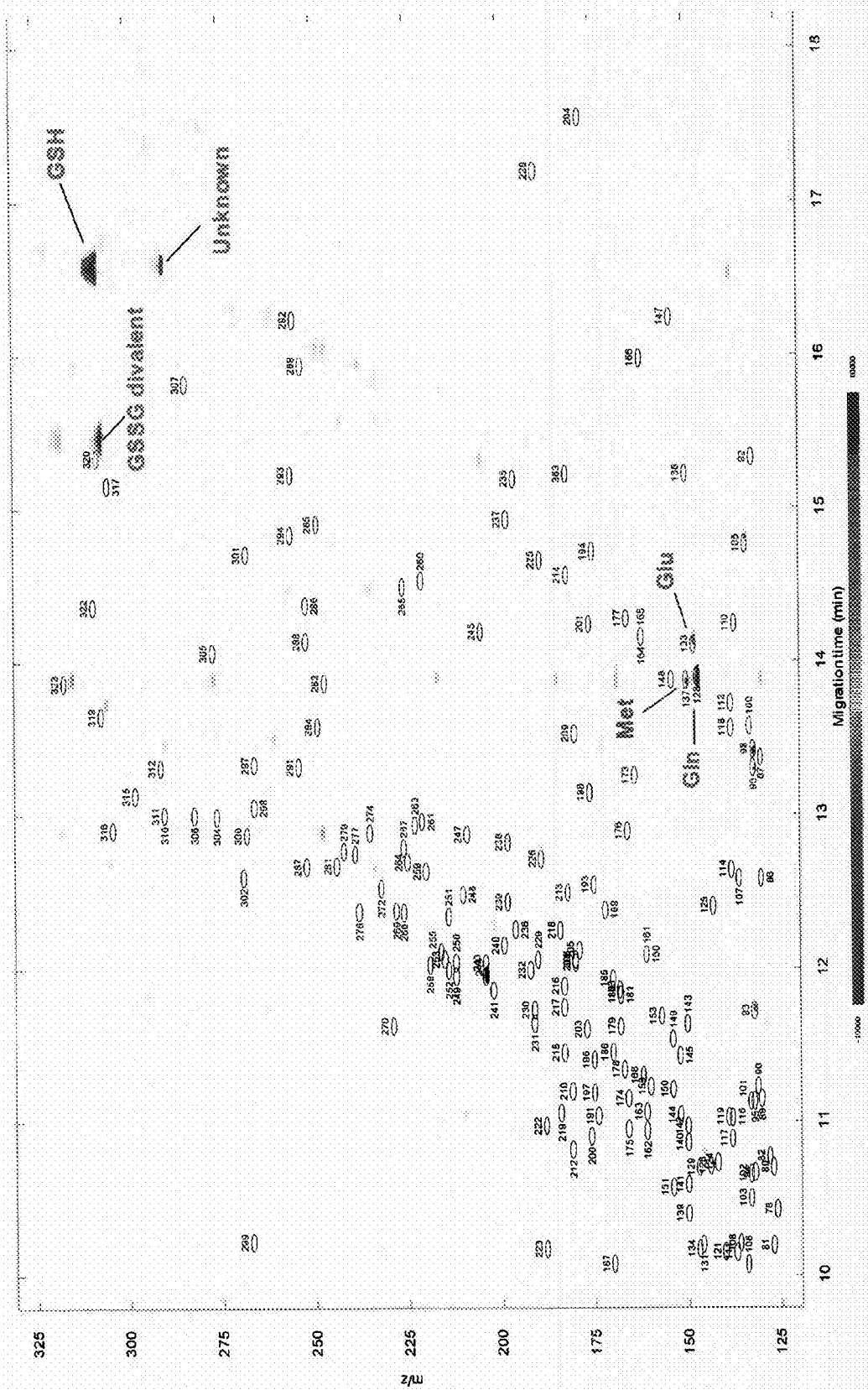
FIG. 1 shows metabolites that varies in liver between control mice and mice at 2 hours after AAP administration. Components increased in mice at 2 hours after AAP administration are shown in red, those decreased in blue.

A method for determination of oxidative stress of the present invention is not particularly limited as long as it is a method of measuring blood concentration of ophthalmic acid, which is a substance that varies in blood depending on the variation of reduced glutathione (GSH) concentration in a biological sample. Further, a screening method for an anti-oxidative stress agent of the present invention is not particularly limited as long as it is a method comprising administering an anti-oxidative stress candidate agent to a non-human animal under oxidative stress conditions, measuring, before and after the administration, blood concentration of ophthalmic acid, which is a substance that varies in blood depending on the variation of reduced glutathione (GSH) concentration in a biological sample, and evaluating the degree of decrease in ophthalmic acid concentration. Examples of the above non-human animal include a mouse, rat, rabbit, canine and feline.

Among ophthalmic acid, γ-Glu-2-aminobutyric acid, oxidized glutathione (GSSG) and the like which are substances that varies in blood depending on the variation of reduced glutathione (GSH) concentration in a biological sample, measurement of blood concentration of ophthalmic acid (e.g., concentration in serum) enables sensitive determination of an oxidative stress or sensitive screening of an anti-oxidative stress agent.

A method for measuring the blood concentration of ophthalmic acid is not particularly limited as long as it is a measuring method using an analyzer such as a capillary electrophoresis-mass spectrometer (CE-MS), high performance liquid chromatography-mass spectrometer (LC-MS), gas chromatography-mass spectrometer (GC-MS), single CE, LC, GC, mass spectrometer (MS), or nuclear magnetic resonance apparatus (NMR). Among these, a measuring method using a capillary electrophoresis-time-of-flight mass spectrometer (CE-TOFMS) is preferred. Measurement of ophthalmic acid in blood using capillary electrophoresis-time-of-flight mass spectrometer can be performed according to a method described in aforementioned Non-Patent Document 1 or the method described in an Example below.

A method for determination of oxidative stress of the present invention is specifically explained as follows. Blood is collected from a test subject. The separated serum is used as a sample and ophthalmic acid concentration in the sample is measured by using, for example, CE-TOFMS. If the obtained value is significantly higher as compared to the value of the test subject in its normal state (when being free of oxidative stress) or the value of a normal individual not under oxidative stress, then the test subject is determined to be under oxidative stress.

When a test subject is determined to be under oxidative stress, an oxidative stress-related disease is suspected. Examples of such disease include cancer, diabetes, arteriosclerosis, obesity, hepatitis, AIDS, Alzheimer's disease, Parkinson's disease, apoptosis, inflammatory response, asthma, eczema, high bone mass syndrome, osteopetrosis, osteoporosis-pseudoglioma syndrome, digestive diseases such as gastric ulcer, irritable bowel syndrome and ulcerative colitis, hypertension, angina pectoris, myocardial infarction, cardiomyopathy, chronic rheumatoid arthritis, musculoskeletal diseases such as migraine and tension headache, respiratory diseases such as bronchial asthma and hyperventilation syndrome, various diabetes complications, and cranial nerve disease.

A method for screening for an anti-oxidative stress agent of the present invention is specifically explained as follows. An anti-oxidative stress candidate agent is administered to a non-human animal such as a mouse under oxidative stress conditions. Ophthalmic acid concentration in serum is measured before and after the administration by using, for example, CE-TOFMS. If the ophthalmic acid concentration in serum after administration is significantly decreased as compared to the ophthalmic acid concentration before the administration, said anti-oxidative stress candidate agent may be possibly used as an anti-oxidative stress agent. Preferably, this screened anti-oxidative stress candidate agent is administered to a non-human animal such as a mouse in its normal state and one that does not change the ophthalmic acid concentration in serum before and after the administration is selected.

Examples of an administration route of the above anti-oxidative stress candidate agent to a non-human animal include injections (e.g., intravenous, intramuscular, subcutaneous, intradermal, and intraperitoneal), oral, transdermal, and inhalation administrations. Formulations may be done appropriately according to these administration routes. In addition, selectable form of an agent can be selected widely from, but not limited to, injectable forms (e.g., solutions, suspensions, emulsions, and solids which will be dissolved in use), tablets, capsules, granules, powders, liquids, liposomals, ointments, gels, powders for external use, sprays, and powders for inhalation. Further, in the preparation of these formulations, components generally used in pharmaceuticals such as commonly used excipients, stabilizers, binders, lubricants, emulsifying agents, osmotic pressure conditioners, pH conditioners, other coloring agents, and disintegrants can be also used. Further, dosage may be selected appropriately.

Examples of a method to place a non-human mammal such as a mouse under oxidative stress conditions include administration of an oxidative stress causing agent such as acetaminophen, exposure to radiation or ultraviolet ray, affection to an infectious disease caused by an environmental pollutant, and exposure to a physically adverse environment such as high fever, low temperature, hypoxic condition, and water immersion restraint.

According to the method for screening of the present invention, an anti-oxidative stress agent effective to an oxidative stress-related disease can be obtained. Examples of such an oxidative stress-related disease include cancer, diabetes, arteriosclerosis, obesity, hepatitis, AIDS, Alzheimer's disease, Parkinson's disease, apoptosis, inflammatory response, asthma, eczema, high bone mass syndrome, osteopetrosis, osteoporosis-pseudoglioma syndrome, digestive diseases such as gastric ulcer, irritable bowel syndrome, and ulcerative colitis, hypertension, angina pectoris, myocardial infarction, cardiomyopathy, chronic rheumatoid arthritis, musculoskeletal diseases such as migraine and tension headache, respiratory diseases such as bronchial asthma and hyperventilation syndrome, various diabetes complications, and cranial nerve disease.

Although the present invention will be illustrated in more detail below with reference to Examples, the technical scope of the present invention is not limited by these exemplifications.

EXAMPLE 1

Sample Preparation from AAP-Administered or Control Mice

Male mice fasted overnight were anesthetized by intraperitoneal injection of pentobarbital sodium (60 mg per Kg body weight). Acetaminophen (AAP), which is an oxidative stress causing agent, or physiological saline as control was injected (150 mg per Kg body weight). At 1, 2, 4, 6, 12 and 24 hours after the AAP administration, liver (about 300 mg) and serum (200 µl) were collected from the mice.

EXAMPLE 2

Metabolites Extraction From Liver

The liver (about 300 mg) harvested from mice was immediately plunged into 1 ml of methanol containing internal standards and homogenized to inactivate enzymes and stop increase in metabolism. Then, 500 µl of pure water was added and 300 µl of the solution was collected. 200 µl of chloroform was added to the solution, which was then thoroughly mixed. The solution was centrifuged at 15000 rpm at 4° C. for 15 minutes. After left standing, the separated 300 µl-water-methanol phase was centrifugally filtered through an ultrafiltration filter (5 kDa cutoff) to remove proteins. The filtrate was lyophilized and 50 µl of MILLI-Q® ultrapure water was added thereto prior to CE-MS (CE-TOFMS) analysis.

EXAMPLE 3

Metabolites Extraction from Serum

Serum (200 µl) was plunged into 1.8 ml of methanol containing internal standards and mixed. Then 800 µl of pure water and 2 ml of chloroform were added, and the solution was centrifuged at 5000 rpm at 4° C. for 5 minutes. After left standing, the separated 800 µl-water-methanol phase was centrifugally filtered through an ultrafiltration filter (5 kDa cutoff) to remove proteins. The filtrate was lyophilized and 50

1 of MILLI-Q® ultrapure water was added thereto prior to CE-MS (CE-TOFMS) analysis.

EXAMPLE 4

Measurement of Metabolites in a Sample with a Capillary Electrophoresis-Time-of-Flight Mass Spectrometer (CE-TOFMS)

Metabolites having a mass of 1000 or less were comprehensively measured using CE-TOFMS under measuring conditions for cationic metabolites and anionic metabolites.
(1) Conditions for Cationic Metabolites Measurement
1) Analytical Conditions of Capillary Electrophoresis (CE)

As a capillary, a fused silica capillary having an inner diameter of 50 μm, an outer diameter of 350 μm, and a total length of 100 cm was used. As a buffer, 1 M formic acid (pH is about 1.8) was used. Measurement was performed with an applied voltage of +30 kV and a capillary temperature of 20° C. A sample was injected at 50 mbar for 3 seconds using the pressure method.
2) Analytical Conditions of Time-of-Flight Mass Spectrometer (TOFMS)

In TOFMS, the positive ion mode was employed and the ionization, fragmentor, skimmer, and Oct RFV voltages were set at 4 kV, 75 V, 50 V, and 125 V, respectively. Nitrogen was used as a drying gas, which was set at a temperature of 300° C. and a pressure of 10 psig. Methanol solution (50%) was used as a sheath liquid. To this solution, reserpine (m/z 609.2807) was added at 0.5 μM for mass calibration and the solution was delivered at 10 μ/min. All the obtained data were automatically calibrated using the mass of reserpine (m/z 609.2807) and methanol adduct ion (m/z 83.0703).
(2) Conditions for Anionic Metabolites Measurement
1) Analytical Conditions of Capillary Electrophoresis (CE)

As a capillary, SMILE(+) capillary having an inner diameter of 50 μm, an outer diameter of 350 μm, and a total length of 100 cm was used. As a buffer, 50 mM ammonium acetate (pH 8.5) was used. Measurement was performed with an applied voltage of −30 kV and a capillary temperature of 20° C. A sample was injected at 50 mbar for 30 seconds using the pressure method.
2) Analytical Conditions of Time-of-Flight Mass Spectrometer (TOFMS)

In TOFMS, the negative ion mode was employed and the ionization, fragmentor, skimmer, and Oct RFV voltage were set at 3.5 kV, 100 V, 50 V, and 200 V, respectively. Nitrogen was used as a drying gas, which was set at a temperature of 300° C. and a pressure of 10 psig. Ammonium acetate (5 mM) in 50% methanol solution was used as a sheath liquid. To this solution, 20 μM PIPES and 1 μM reserpine (m/z 609.2807) was added for mass calibration and was delivered at 10 μ/min. All the obtained data were automatically calibrated using the mass of reserpine (m/z 609.2807), monovalent PIPES (m/z 301.0534), and divalent PIPES (m/z 150.0230).

EXAMPLE 5

Finding of Ophthalmic Acid as a Biomarker for Oxidative Stress and Drug Stress Metabolites were extracted over time from liver and blood of control mice and mice which had received an excessive administration of AAP, which is an oxidative stress causing agent, to induce hepatocyte necrosis. The extracts were comprehensively and quantitatively analyzed with a capillary electrophoresis-mass spectrometer (CE-MS) or the like. At 2 hours after AAP administration, hepatocyte necrosis was observed. FIG. 1 shows the components increased or decreased in the liver when the control mice and the mice 2 hours after AAP administration were compared. Red points show increased substances and blues show decreased substances in the mice 2 hours after AAP administration. Dramatically decreased substances are GSH and oxidized glutathione (GSSG). Furthermore, an unknown substance having a mass of 290 which was detected at the same time point as GSH was increased by AAP administration. The accurate mass obtained from CE-TOFMS and the structural information obtained from CE-MS/MS leads to speculation that this substance is ophthalmic acid (γ-Glu-2ABs-Gly), in which Cys in the middle of GSH (γ-Glu-Cys-Gly) is substituted with 2-aminobutyric acid (2-aminobutyrate (2AB)). Ophthalmic acid preparation was obtained and compared with the unknown substance. As estimated, the unknown substance was ophthalmic acid.

Figure 2:
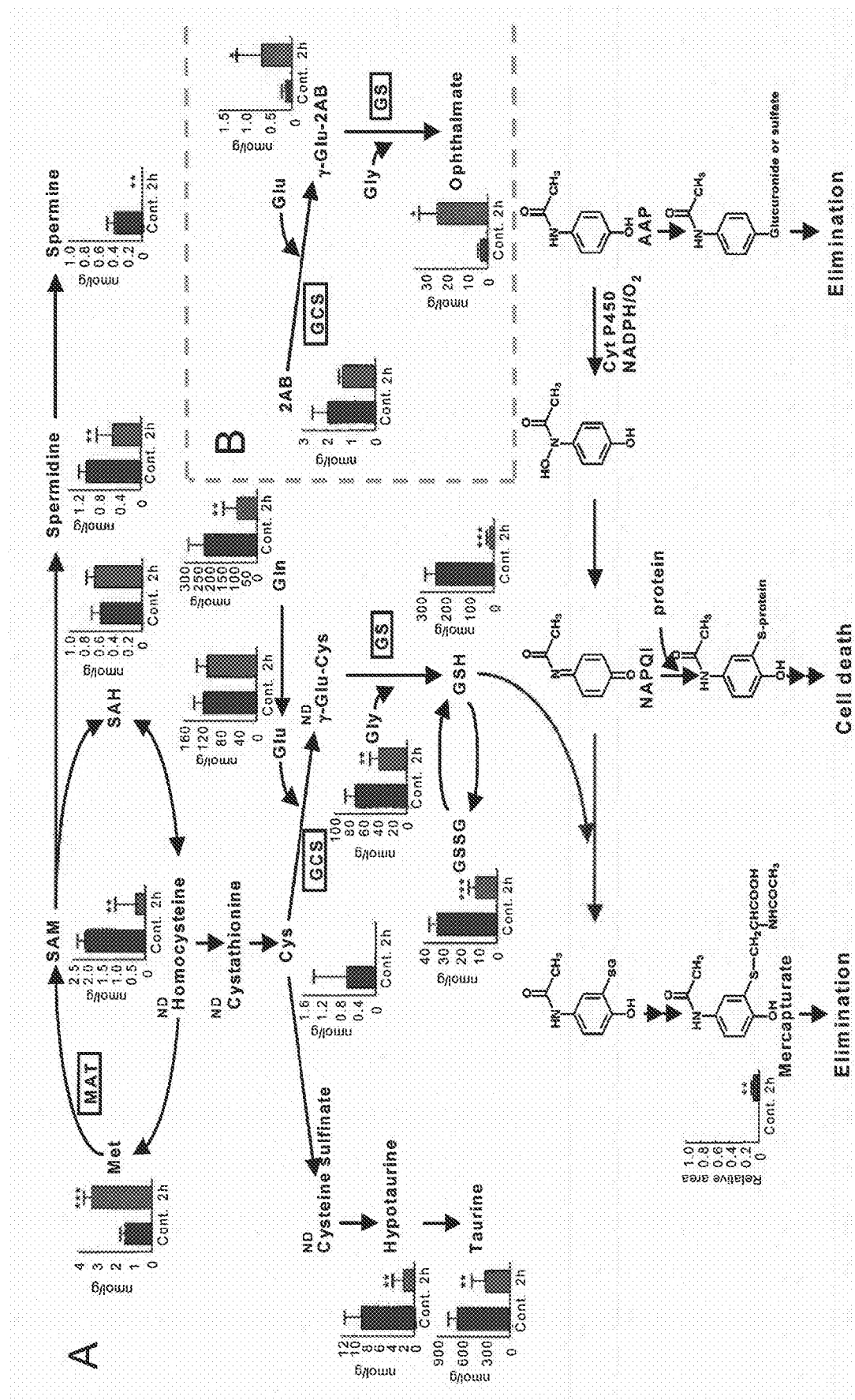
FIG. 2 shows quantitative values of metabolites in liver of control mice and mice at 2 hours after AAP administration. The quantitative values of metabolites in control mice are shown in blue, those in mice at 2 hours after AAP administration are shown in red. Results of t test for quantitative values of control mice and AAP-administered mice (*$p<0.001$, $p<0.01$, *$p<0.05$). A) Substances in AAP metabolism pathway. B) Substances in ophthalmic acid biosynthesis pathway.

As shown in FIG. 2A, hepatocyte necrosis by AAP administration is because some of AAP are metabolized by cytochrome P450 to produce the toxic substance NAPQI, which binds to an SH group of various proteins (oxidation). Typically, NAPQI is bound by GSH and is excreted into urine. If GSH is depleted, however, NAPQI binds to proteins and causes cell necrosis. Comparison of concentration variations of each metabolite measured by CE-TOFMS (FIG. 2A) shows decrease in all the substances in the glutathione biosynthesis pathway in the liver of mice 2 hours after AAP administration compared to the control. On the other hand, increase in γ-Glu-2-aminobutyric acid (γ-Glu-2AB), which is produced by glutathione synthesis pathway enzymes of glutamyl cysteine synthetase (GCS) and glutathione synthetase (GS), and increase in ophthalmic acid were observed.

Figure 3:
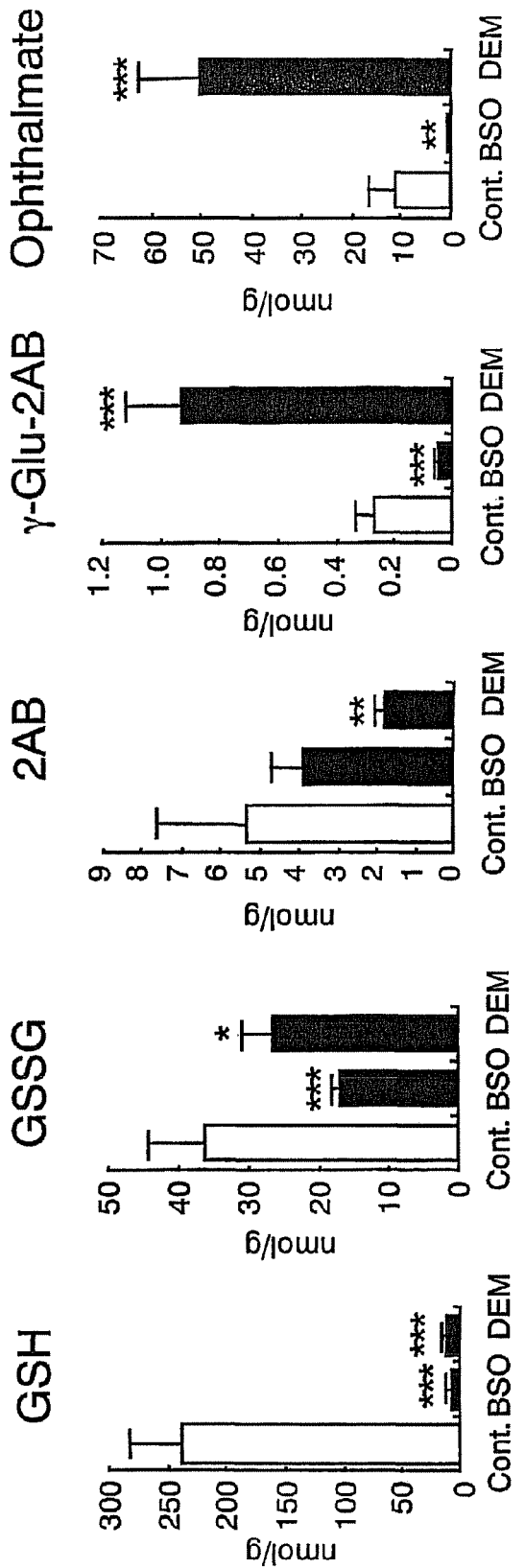
FIG. 3 shows quantitative values of metabolites in liver of control mice and mice at 2 hours after BSO or DEM administration. Results of analyzing quantitative values of control mice and agent-administered mice for statistically significant difference (t test) (*$p<0.001$, $p<0.01$, *$p<0.05$).

Further, the present inventors have elucidated this metabolism mechanism by administering BSO (buthionine sulfoximine), which inhibits GCS, or DEM (diethylmaleate), an agent that causes oxidative stress as AAP does, to mice. BSO is feedback-inhibited by GSH and inhibits the activity of GCS, the rate-limiting enzyme of glutathione synthesis pathway. Therefore, γ-Glu-Cys, GSH (FIG. 2A), γ-Glu-2AB, and ophthalmic acid (FIG. 2B), which are downstream metabolites of GCS, were remarkably decreased. Further, as seen with AAP administration, the depletion of GSH and increase in γ-Glu-2AB and ophthalmic acid were observed in DEM administration (FIG. 3). These results confirmed that GSH depletion by AAP administration activates GCS, which led to biosynthesis of ophthalmic acid from a substrate 2AB through γ-Glu-2AB (FIG. 2B). GCS activation also leads to GSH synthesis using Cys as a substrate. However, GSH level is not recovered because either 1) GSH is consumed in reaction with NAQPI, or 2) Cys does not exist sufficiently for GSH synthesis. However, ophthalmic acid was accumulated in cells because it does not react with NAPQI unlike GSH. Further, GSSH showed almost the same variation pattern as that of GSH.

Figure 4:
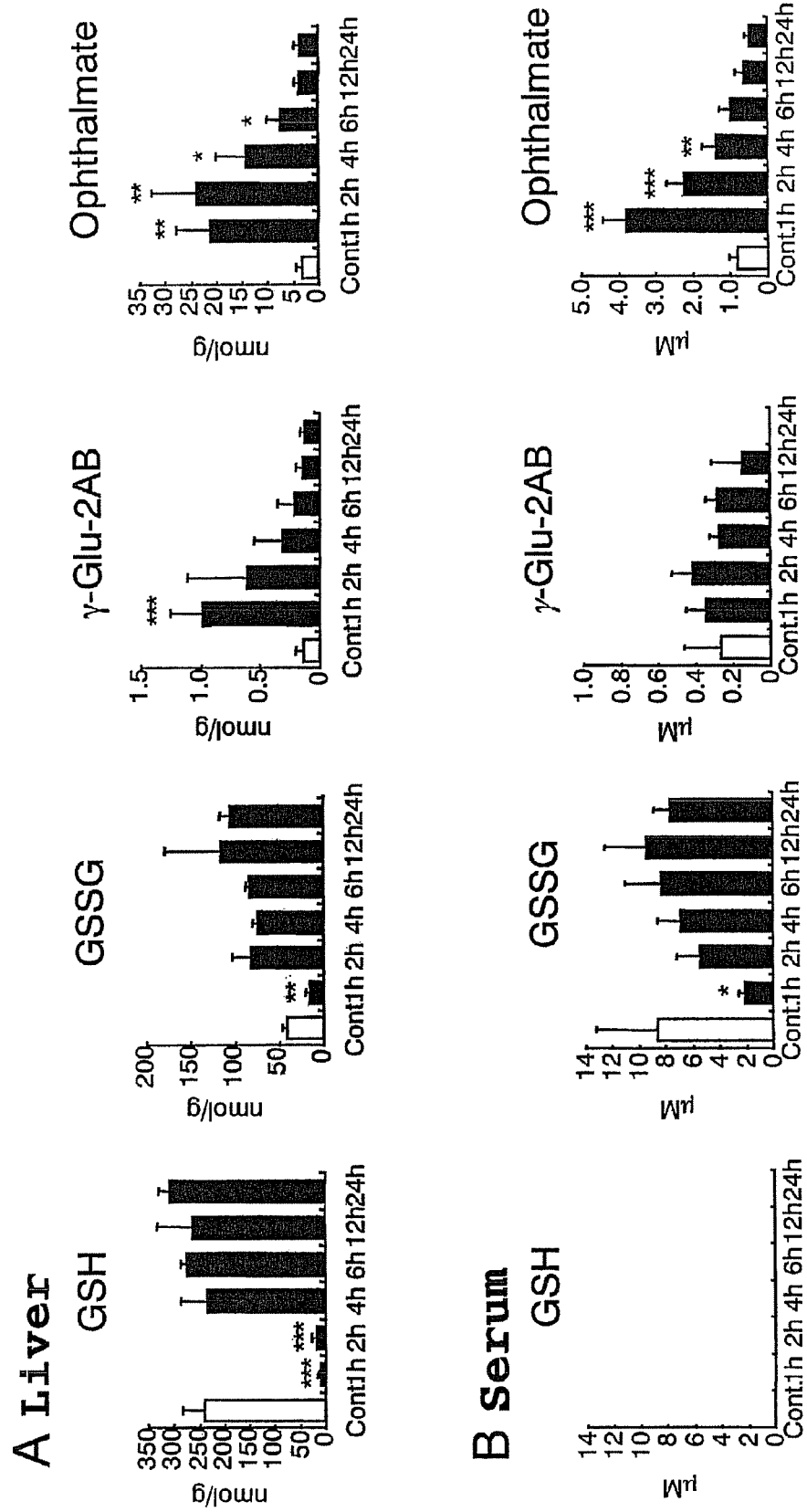
FIG. 4 shows change of quantitative values of metabolites of mice after AAP administration over time in A) liver and B) serum. Results of t test against control quantitative values (*$p<0.001$, $p<0.01$, *$p<0.05$).

These results revealed that GSSG, γ-Glu-2AB, and ophthalmic acid in liver largely varies responding to the GSH decrease by AAP- or DEM-caused oxidative stress. If these substances in blood also respond to the GSH decrease, these can be used as a biomarker. Accordingly, AAP was administered to mice and concentrations of these substances in liver and serum at 1, 2, 4, 6, 12, and 24 hours after the administration were measured and compared (FIG. 4).

At 1 and 2 hours after AAP administration, when hepatic necrosis occurs, GSH in liver was rapidly decreased. In serum, however, GSH was not detected. GSSH in liver and serum showed a behavior similar to that of GSH in liver.

Ophthalmic acid in liver and serum showed a behavior opposite from that of GSH in liver. In addition, at 1 and 2 hours after the administration, when GSH rapidly decreased in liver, ophthalmic acid was dramatically increased and statistically significant difference from the control mice was also large. From the above, since ophthalmic acid has a high blood concentration and rapidly increases by sensing the GSH decrease in liver, ophthalmic acid was proved to be an effective biomarker reflecting redox regulation state in liver.

INDUSTRIAL APPLICABILITY

Ophthalmic acid (ophthalmate) in blood found in the present invention rapidly increases by promptly sensing oxidative stress caused by an agent, radiation, ultraviolet ray, environmental pollutant, high fever, low temperature, hypoxic condition, infectious disease, etc. Therefore it is not only useful for determination and diagnosis of oxidative stress, but also may be used as a marker of drug toxicity and efficacy for oxidative stress. Further, ophthalmic acid in blood may be able to sense oxidative stress seen in cancer, diabetes, arteriosclerosis, obesity, hepatitis, AIDS, Alzheimer's disease and the like and may be used for early detection of these diseases.

The invention claimed is:

1. A method for screening for an anti-oxidative stress agent, comprising:

administering an anti-oxidative stress candidate agent to a non-human animal under oxidative stress conditions;

measuring, before and after the administration, blood concentration of ophthalmic acid, which is a substance that varies in blood depending on the variation of reduced glutathione (GSH) concentration in a biological sample; and evaluating the degree of decrease in ophthalmic acid concentration.

2. The method for screening for an anti-oxidative stress agent according to claim 1, wherein the anti-oxidative stress agent is a therapeutic agent for an oxidative stress-related disease selected from the group consisting of cancer, diabetes, arteriosclerosis, obesity, hepatitis, AIDS, and Alzheimer's disease.

3. The method for screening for an anti-oxidative stress agent according to claim 1, wherein the blood concentration of ophthalmic acid is measured with a capillary electrophoresis-mass spectrometer.

4. The method for screening for an anti-oxidative stress agent according to claim 1, wherein the anti-oxidative stress agent is a therapeutic agent for an oxidative stress-related disease selected from the group consisting of cancer, diabetes, arteriosclerosis, obesity, hepatitis, AIDS, and Alzheimer's disease.

* * * * *

UNITED STATES PATENT AND TRADEMARK OFFICE
CERTIFICATE OF CORRECTION

PATENT NO. : 7,964,177 B2
APPLICATION NO. : 12/161203
DATED : June 21, 2011
INVENTOR(S) : Tomoyoshi Soga et al.

It is certified that error appears in the above-identified patent and that said Letters Patent is hereby corrected as shown below:

In claim 4, at column 10, lines 20-25:  Replace

"The method for screening for an anti-oxidative stress agent according to claim 1, wherein the anti-oxidative stress agent is a therapeutic agent for an oxidative stress-related disease selected from the group consisting of cancer, diabetes, arteriosclerosis, obesity, hepatitis, AIDS, and Alzheimer's disease."

with

--The method for screening for an anti-oxidative stress agent according to claim 3, wherein the anti-oxidative stress agent is a therapeutic agent for an oxidative stress-related disease selected from the group consisting of cancer, diabetes, arteriosclerosis, obesity, hepatitis, AIDS, and Alzheimer's disease.--

Signed and Sealed this
Sixteenth Day of August, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,964,177 B2 | Page 1 of 1 |
| APPLICATION NO. | : 12/161203 | |
| DATED | : June 21, 2011 | |
| INVENTOR(S) | : Soga et al. | |

It is certified that error appears in the above-identified patent and that said Letters Patent is hereby corrected as shown below:

Title page, item [56], under OTHER PUBLICATIONS, in Murata, replace
"Protein, Nucleic Acid and Enzyme" with --*Protein, Nucleic Acid and Enzyme*--.

Column 7, Line 1, replace "1 of MILLI-Q® ultrapure water" with
--μl of MILLI-Q® ultrapure water--.

Signed and Sealed this
First Day of January, 2013

David J. Kappos
*Director of the United States Patent and Trademark Office*